United States Patent
Lewandrowski et al.

(10) Patent No.: US 7,534,419 B2
(45) Date of Patent: May 19, 2009

(54) METHODS OF DIAGNOSIS AND TREATMENT OF OSTEOPOROSIS

(75) Inventors: Kai-Uwe Lewandrowski, Brookline, MA (US); Debra J. Trantolo, Princeton, MA (US)

(73) Assignee: Depuy Mitek, Inc., Raynham, MA (US)

( * ) Notice: Subject to any disclaimer, the term of this patent is extended or adjusted under 35 U.S.C. 154(b) by 1345 days.

(21) Appl. No.: 10/054,171

(22) Filed: Jan. 17, 2002

(65) Prior Publication Data
US 2002/0137082 A1  Sep. 26, 2002

Related U.S. Application Data

(60) Provisional application No. 60/263,109, filed on Jan. 19, 2001, provisional application No. 60/304,887, filed on Jul. 12, 2001.

(51) Int. Cl.
*A61K 49/00* (2006.01)
*A61K 39/00* (2006.01)

(52) U.S. Cl. ............. 424/9.1; 424/140.1; 424/549; 435/6; 435/7.94

(58) Field of Classification Search .......... 435/7.21, 435/7.1, 6, 7.94; 424/9.1, 140, 549
See application file for complete search history.

(56) References Cited

U.S. PATENT DOCUMENTS

| | | | |
|---|---|---|---|
| 5,232,833 | A | 8/1993 | Sanders et al. |
| 5,780,246 | A | 7/1998 | Sanders et al. |
| 5,830,464 | A | 11/1998 | Srivastava |
| 5,948,646 | A | 9/1999 | Srivastava |
| 5,985,270 | A | 11/1999 | Srivastava |
| 6,030,618 | A | 2/2000 | Srivastava |

FOREIGN PATENT DOCUMENTS

| | | |
|---|---|---|
| EP | 0 557 663 | 9/1993 |
| WO | WO 00/13024 | 3/2000 |
| WO | WO 00/22437 | 4/2000 |

OTHER PUBLICATIONS

Reddi, et al., "The *Escherichia coli* chaperonin 60 (groEL) is a potent stimulator of osteoclast formation," J. Bone Min. Res. 13(8): 1260-1266 (1998).
Nair, et al., "Molecular chaperones stimulate bone resorption," *Calcified Tissue International* 64(3): 214-218 (1999).
Bardwell, et al., "Major heat shock gene of *Drosophila* and the *Escherichia coli* heat-inducible dnaK gene are homologous" *Proc. Natl. Acad. Sci. USA* 81(3):848-852 (1984).
Black, et al., "Axial and appendicular bone density predict fractures in older women" *J. Bone Miner Res.* 7(6):633-638 (1992).
Consensus Development Center, "Prophylaxis and treatment of osteoporosis" *Am J Med.* 90:107-110 (1991).
Cummings, et al., "Bone density at various sites for prediction of hip fractures. The Study of Osteoporotic Fractures Research Group" *Lancet* 341(8837):72-75 (1993).
Elffors, "Are osteoporotic fractures due to osteoporosis? Impacts of a frality pandemic in an aging world," *Aging* (Milano) 10(3): 191-204 (1998).
Gallagher, et al., "Epidemiology of fractures of the proximal femur in Rochester, Minnesota" *Clin. Orthop.* 150:163-171 (1980).
Genant, et al., "Measurement of bone mineral density: current status" *Am J. Med.* 9I (5B):49S-53S (1991).
Greenberg, et al. "Comparison of labeled heat shock proteins in neuronal and non-neuronal cells of *Aplysia californica*." *J. Neuroscience* 5(5):1239-45 (1985).
Helgeland, et al., "Cell cycle-specific growth inhibitory effect on human gingival fibroblasts of a toxin isolated from the culture medium of *Actinobacillus actinomycetemcomitans*," *J. Periodontal. Res.*, 28(3): 161-165 (1993).
Horiguchi et al., "Effect of *Bordetella bronchiseptica* dermonecrotic toxin on the structure and function of osteoblastic clone MC3T3-e1 cells," *Infect. Immun.*, 59(3): 1112-1116 (1991).
Kanis, et al., "The diagnosis of osteoporosis," *J Bone Miner Res*, J Bone Miner Res, 9(8):1137-41 (1994).
Kimman et al., Stimulation of bone resorption by inflamed nasal mucosa, dermonecrotic toxin-containing conditioned medium from *Pasteurella multocida*, and purified dermonecrotic toxin from *P. multocida*, *Infect. Immun.*, 55:2111-2116 (1987).
Larjava, et al., "Inhibition of gingival growth by *Bacteroides gingivalis*," *Infect. Immun.*, 55(1):201-205 (1987).
Lindquist, et al., "The heat-shock proteins" *Ann. Rev. Genetics* 22:631-677 (1988).
Livneh, et al., "Chronic gonococcal arthritis," *J. Rheumatol.*, 16: 115-121 (1983).
Meghji, et al., "Inhibition of bone DNA and collagen production by surface-associated material from bacteria implicated in the pathology of periodontal disease" *J. Periodontol*. 63(9):736-742 (1992).
Meghji, et al., "Anti-proliferative and cytotoxic activity of surface-associated material from periodontopathogenic bacteria," *Arch. Oral Biol.*, 37(8):637-644 (1992).

(Continued)

Primary Examiner—Gina C Yu

(57) ABSTRACT

A method of detecting osteoporosis in a mammalian is disclosed herein which includes:
a) obtaining a sample of a bone related tissue or cells; and
b) measuring the concentration of at least a marker which is either bacteria, bacteria produced factors, or HSPs. The method may further include comparing the concentration with concentrations from the same individual over a period of time or against a standard concentration. The marker may be a bacteria, a chaperone molecule, or a bacteria produced. Also provided herein is a method of treating or preventing osteoporosis caused by a bone disease which includes administering to a mammalian subject a therapeutically effective amount of a formulation which is either an HSP antigenic formulation or a bacterial antigenic formulation. The osteoporosis can be caused by a bone disease induced by bone infectious agents such as viruses, bacteria, fungi, protozoa and parasites.

12 Claims, No Drawings

OTHER PUBLICATIONS

Melton et al., "Long-term fracture prediction by bone mineral assessed at different skeletal sites" *Bone Miner Res.* 8(10):1227-1233 (1993).

Melton, et al., "Epidemiology of vertebral fractures in women" *Am. J. Epidemiol.* 129(5):1000-1011 (1989).

Millar, et al., "Modulation of bone metabolism by two chemically distinct lipopolysaccharide fractions from *Bacteroides gingivalis*" *Infect. Immun.* 51 (1): 302-306 (1986).

Multanen, et al., "Inhibition of bone collagen synthesis by dental plaque extracts," *J. Clin. Periodontol.* I:729-739 (1985).

Nair, et al., "Molecular chaperones stimulate bone resorption" *Calcif Tissue Int* 64 (3):214-8 (1999).

Ross, "Infected arthroplastics," *Curr. Opin. Rheumatol.*, 3(4):628-633 (1991).

Ryden, et al., "Specific binding of bone sialoprotein to *Staphylococcus aureus* isolated from patients with osteomyelitis" *Eur. J Biochem.* 184(2): 331-336 (1989).

Silveira, et al., "Ultrastructural changes in the nasal turbinate bones of pigs in early infection with *Bordetella bronchiseptica*," *Res Vet Sci* 33(1):37-42 (1982).

Srivastava, et al., "Stress-induced proteins in immune response to cancer" *Curr. Topics in Microbiology & Immun.* 167:109-123 (1991).

Wilson, "Biological activities of lipopolysaccharides from oral bacteria and their relevance to the pathogenesis of chronic periodontitis" *Sci. Prog.* 78(PT1):19-34 (1995).

Wilson, et al., "Bone resorbing activity of purified capsular material from *Actinobacillus actinomycetemcomitans*," *J. Periodontal. Res.* 20(5): 484-491 (1985).

METHODS OF DIAGNOSIS AND TREATMENT OF OSTEOPOROSIS

The U.S. Government has rights to this application by virtue of a Grant from the National Institutes of Health.

FIELD OF THE INVENTION

This application claims priority to U.S. Ser. No. 60/263,109 entitled "Methods of Using Heat Shock Proteins for Diagnosis and Treatment of Bone Disease" filed Jan. 19, 2001 by Kai-Uwe Lewandrowski and U.S. Ser. No. 60/304,887 entitled "Methods of Diagnosis and Treatment of Osteoporosis" filed Jul. 12, 2001 by Kai-Uwe Lewandrowski.

The present application generally relates to methods for diagnosing bone loss. More specifically, the present application relates to identifying humoral markers for bone loss on the basis of bacterial or mammalian molecular chaperones.

BACKGROUND OF THE INVENTION

Osteoporosis is a systemic disorder characterized by decreased bone mass and microarchitectural deterioration of bone tissue leading to bone fragility and increased susceptibility to fractures of hip, spine, and wrist. Osteopenia has been defined as the appearance of decreased bone mineral content on radiography, but the term more appropriately refers to a phase in the continuum from decreased bone mass to fractures and infirmity. By the time the diagnosis of osteopenia is made radiographically, significant and irreversible bone loss has already occurred. The most common cause of osteopenia is osteoporosis; other causes include osteomalacia and the bone disease of hyperparathyroidism.

In the United States, roughly 1 in 4 women over the age of 50 has osteoporosis. The overall prevalence of osteoporotic fractures rises dramatically in menopausal women. Bone loss is more abrupt for the first decade after the onset of menopause, followed by more gradual loss thereafter (Nordin, et al., "How can we prevent osteoporosis?" in Osteoporosis, Christiansen, et al., (eds). Copenhagen, Norhaven A/S, 1204-1210 (1987)). With increasing age, fracture incidence increases. The frequency of hip fractures increases exponentially with age, particularly after age 70, and is more commonly seen in white women. About 32% of women who live to age 80 have hip fractures (Gallagher, et al., Clin. Orthop. 150:163-171 (1980); Melton, et al., Am. J. Epidemiol. 129: 1000-1011 (1989)). A woman's risk of a hip fracture equals the combined risk of breast, uterine, and ovarian cancer, and the risk of dying of hip fracture is equal to breast cancer mortality (Elffors, Aging (Milano) 10:191-204 (1998)). The prevalence of vertebral fractures is 42% in women of advanced age and/or who have decreased bone mass (Melton et al., 1989). In women, a rapid rise of vertebral fractures, which is initially associated with the onset of menopause, is followed by an increase in the frequency of wrist and hip fractures due to age-related bone loss.

Osteoporosis develops less often in men than women because bone loss starts later and progresses more slowly in men, and there is no period of rapid hormonal change and accompanying rapid bone loss. Differences in bone geometry and remodeling also contribute to the lower rate of fractures in men. However, in the past few years, the problem of osteoporosis in men has become recognized as an important public health issue, particularly in light of estimates that the number of men older than 70 will double between 1993 and 2050 according to the US National Osteoporosis Foundation.

Roughly 1 in 8 men over the age of 50 years has osteoporosis. Presently, more than 2 million men in the United States are affected by osteoporosis, and another 3 million are at risk for this disease. Each year, men have one third of all hip fractures that occur, and one third of these men will not survive more than a year. The frequency of hip fracture increases exponentially with age, particularly after age 70, and 17% of men who live to age 80 have hip fractures (Gallagher et al., 1980; Melton et al., 1989). In addition to hip fracture, men also have painful and debilitating fractures of the spine, wrist, and other bones due to osteoporosis.

While the damages caused by osteoporosis are severe and are sometimes fatal, no exact clinical chemical tests on blood or urine are abnormal in osteoporosis. Currently used techniques are generally biochemical markers, radiography, and measurement of bone mineral density (BMD). The use of these techniques is limited either by cost or by accuracy reasons.

It is an object of the present invention to provide an effective means for evaluation of environmental and bone infectious stresses on the skeletal system.

It is a further object of the present invention to provide a means for treating and/or preventing infectious disorders having a negative impact on the skeletal system.

SUMMARY OF THE INVENTION

A method of detecting osteoporosis in a mammal has been developed. The method includes the steps of a) obtaining a sample of a bone related tissue or cells; and b) measuring the concentration of at least a marker which is one of bacteria, bacteria produced factors, or heat shock proteins (HSPs). The method may further include comparing the concentration of a first assay with concentrations of a second or more assays from the same individual over a period of time or against a standard concentration. The marker can an HSP such as HSP 70, HSP 60, HSP 90, gp 96, cpn10, cpn20, ubiquitin or cpn 30. The marker can also be a bacteria such as *Staphylococcus aureus, Porphyromonas gingivallis, Eikenella corrodens, Actinobacilus actinomycetemcomitans, Prevotella intermedia, Campylobacter rectus, Staphylococcus epidermidis, Salmonella* spp., *Escherichia coli, Neisseria gonorrhoea, Neisseria meningitis, Mycobacterial tuberculosis, Haemophius influenzae, Pasteurella multocida, B. bronchiseptica,* or *Fusobacterium nucleatum.* The marker may be a bacteria produced factor such as endotoxin-LPS, gapstatin, and dermonecrotic toxin (DNT). The time between assays may extend over a period, for example, of at least about 12 hours. In one embodiment, the concentration of HSP is measured using an immunoassay. In another embodiment, the concentration of HSP is measured using an assay for a nucleotide molecule encoding HSP.

A method of treating or preventing osteoporosis has been developed. A therapeutically effective amount of a formulation which is either an HSP antigenic formulation or a bacterial antigenic formulation. In one embodiment, the osteoporosis is caused by a bone disease induced by bone infectious agents such as viruses, bacteria, fungi, protozoa or parasites. The HSP can be HSP 60, HSP 70, HSP 90, gp 96, cpn 10, cpn 20, ubiquitin, or cpn 30, or combinations thereof. The HSP can be further complexed with an antigenic material or formulated in combination with an adjuvant. The antigenic material can be a peptide or a protein having an antigenic determinant of a virus, bacteria, fungi, protozoa or parasite that induces a bone disease.

The methods disclosed herein can be practiced using a kit formed according to the methods disclosed herein.

DETAILED DESCRIPTION OF THE INVENTION

I. Definitions

The term molecular chaperone describes a number of unrelated proteins that are involved in the assembly and reassembly of proteins and in the transmembrane transport of proteins, for example, from the cytoplasm into the mitochondria. Some of these proteins are referred to as heat shock proteins ("HSPs") or stress proteins. Representative HSPs include HSP 70, HSP 70, gp 96, and HSP 100. These HSPs accomplish different kinds of chaperonin functions. For example, HSP 70, located in the cell cytoplasm, nucleus, mitochondria, or endoplasmic reticulum, (Lindquist, S., et al., 1988, Ann. Rev. Genetics 22:631-677) is involved in the presentation of antigens to the cells of the immune system, and is also involved in the transfer, folding and assembly of proteins in normal cells. HSP 70 located in the cytosol is involved in similar activities. GP 96 present in the endoplasmic reticulum is alao involved in antigen presentation (Srivastava, P. K., et al., 1991, Curr. Topics in Microbiology & Immun. 167:109-123).

HSPs are essential to both prokaryotic and eukaryotic cells for chaperone function during the intracellular (un)folding, assembly and translocation of proteins. By definition, HSP expression is elevated in cells undergoing stress, such as those in damaged or inflamed tissue. Conditions as diverse as a rise in temperature, hypoxia, irradiation, infection and exposure to toxic chemicals can all result in increased HSP expression.

Upon exposure to a stressor, three distinct events result in a rapid change in metabolic activities within the cell: (1) there is increased transcription of HSP mRNAs which are then preferentially translocated to a cytoplasm, (2) the transcription of most other mRNAs is suppressed; and (3) the normal translational activities of the ribosomes are disrupted so that HSPs are preferentially translated. The overall result of these events is that the cell rapidly begins synthesizing HSPs and represses the synthesis of other peptides. No new peptides or RNA synthesis is necessary to activate the translation of the heat shock peptide genes, indicating that preexisting factors, such as viral or bacterial agents, may be involved. Cell type, state of cell differentiation, type of stressor, and the duration and intensity of stress can affect the quantity and quality of a particular type of HSP.

Within the HSP families, individual members have a unique degree of sequence homology. For HSP 60, the human protein has 50% sequence identity with the mycobacterial homologue, with a further 20% conservative substitutions, causing several areas in the human molecule to be fully identical to the bacterial protein. Despite their high degree of conservation, HSPs are very immunogenic. The potential of HSPs for inducing autoimmunity has been broadly investigated. However, induction of autoimmunity was not reported in most experimental systems. Rather, in many models of experimental autoimmune diseases, development of resistance to subsequent induction of a disease is a common feature.

In recent years, it has become clear that HSPs are constitutive molecules. A number of HSPs are well known proteins, including ubiquitin, immunosuppressant-binding proteins and P-glycoprotein. HSPs have been reported to induce cell and tissue behavior consonant with their involvement in inflammation. HSP 70 and *E. coli* groEL induce pores in membranes and thus may have similar actions to a wide variety of lysins and haemolysins produced by bacteria. There are now a number of reports that HSPs from various bacteria can induce human or murine cells to release a range of pro-inflammatory cytokines.

Efforts have been directed to develop ways to make use of HSPs. For example, methods of evaluating chronic exposure of a mammal to sublethal levels of pollutants by measuring HSP concentrations have been reported. See, for example, U.S. Pat. Nos. 5,780,246; 5,232,833, both to Sanders, et al. Compositions and methods of vaccinating with HSPs to prevent diseases such as cancers have been developed. See, for example, U.S. Pat. Nos. 5,830,464; 5,948,646; and 6,030,618, all to Srivastava.

An "antigenic molecule" as used herein refers to peptides with which the HSPs are endogenously associated in vivo (e.g., in infected cells) as well as exogenous antigens/immunogens (i.e., with which the HSPs are not complexed in vivo) or antigenic/immunogenic fragments and derivatives thereof.

"Specifically hybridize" as used herein refers to nucleotide molecules which hybridize with the mRNA transcribed from the gene for the HSP at a stringency condition wherein selected number of base-pair mismatches results in nonhybridization. One skilled in the art will recognize the stringency conditions for various hybridization assay formulas depend upon the constellation of temperature, ionic concentration and pH. Generally, for optimal RNA:RNA hybridization, the temperature is inversely related to the salt concentration; the pH should be held in the range of from about 6.9 to about 7.4, e.g., for 15 nucleotide sequences (15-mer). For RNA:DNA hybridizations, similar assay conditions apply but lower temperatures (accompanied by higher salt concentrations) are generally employed than for RNA:RNA hybridizations.

SDS-PAGE is a common tool for protein analysis. Sodium dodecyl sulfate is a detergent that coats proteins with negative charges at a constant charge-to-mass ratio such that in an electric field the proteins would travel at the same velocity in the absence of any separation matrix. However, when the charged proteins are loaded onto a porous polyacrylamide gel and an electric field is applied, the smaller proteins are able to travel faster through the gel to the anode (+) than larger proteins, which encounter more resistance traveling through the gel. There are different types of stains that can be used to develop the gel, such as Coomassie blue and Silver stain. In many cases SDS-PAGE is a qualitative tool, in which the rough quantities and sizes of proteins in a sample can be gauged by direct comparison of the band in question to bands of a molecular weight ladder.

The Agilent Bioanalyzer™ is a micro-total analysis system (p-TAS) that uses miniaturized chemical chips with microchannel networks fabricated on glass, quartz, or plastic chips. A typical channel is roughly 50 microns wide and 10 microns deep. The Agilent Bioanalyzer™ Protein 200 Assay was developed to more efficiently characterize proteins by size and concentration in a sample. This microfluidic system functions somewhat analogously to SDS-PAGE, but confers many benefits over the macro-scale analytical method. Some advantages of the Protein 200 Assay for the Bioanalyzer™ include small sample volumes, higher throughputs of data/sample, reduced resource consumption and waste production, and automation of multi-step processes.

In the Protein 200 Assay, proteins are denatured with B-mercaptoethanol and fluorescence labeled. In addition, as in SDS-PAGE, the proteins are coated with SDS at a constant charge-to-mass ratio. Strategically located electrodes create electrokinetic forces capable of moving fluids and separating different sized proteins. The molecules are separated by the amount of charge on the protein. Larger, more negatively charged proteins travel toward the cathode. As labeled protein molecules migrate past a certain point in the channel, their fluorescence is detected by a laser beam. The sensitivity of the Protein 200 Assay is known to be affected by salt concentrations in the sample buffer because at higher concentrations smaller amounts of protein are injected into the separation channel.

II. Diagnostic Techniques for Osteoporosis

No exact clinical chemical tests on blood or urine are abnormal in osteoporosis, but biochemical markers, radiography, and measurement of bone mineral density (BMD) are helpful in diagnosing osteoporosis. Bone mass density testing is used to diagnose osteoporosis, and x-ray films are used to rule out other bone or arthritic conditions. Thin bones may be detected on an x-ray film, but bone density testing is more accurate.

A. Bone Densitometry

Considerable progress in the development of methods for assessing skeletal bone mass now makes it possible to detect osteoporosis noninvasively and early. Generally, osteoporosis may be detected after fractures that occur with minimal trauma, as an incidental finding on an x-ray film, or by measurement of BMD by bone densitometry, which is also known as bone density scans. Bone density scans are considered by many as an instant snapshot of bone status. These scans, known collectively as BMD tests, are used to detect the amounts of bone mass in the spine, hip, wrist, hand, heel, or the entire body and to evaluate its density. Some studies have indicated that information regarding bone-mineral content at any anatomic site is equally valuable for predicting the risk of fracture in general (Black, et al., J. Bone Miner Res. 7:633-638 (1992); Melton, et al., J. Bone Miner Res, 8, 1227-1233 (1993)), but other studies have suggested that measurements obtained at a particular site of interest may provide the most important information for the prediction of fracture at that site (Cummings, et al., Lancet 341:72-75 (1993)). Bone mineral density tests are the most sensitive and specific tests for osteopenia are essential in predicting the risk of fracture.

Several techniques are available to measure BMD noninvasively. All of today's x-ray based measurement systems are precise and deliver extremely low, effective radiation doses. The main advantages of an x-ray system over a radionuclide system are safe, shortened examination time, greater accuracy and precision limited to high resolution, and removal of errors due to source decay correction. The variety of bone scan techniques that are widely used today include single x-ray absorptiometry, dual energy x-ray absorptiometry (DEXA), quantitative computed tomography, peripheral quantitative computed tomography, radiographic absorptiometry, quantitative ultrasound, simple photon absorptiometry, and dual photon absorptiometry. Their development has been driven by the need to overcome the inherent shortcomings of plain radiography for this purpose. Although single and dual photon absorptiometry are still available, these older techniques are rapidly being replaced by single x-ray absorptiometry and DEXA, their modern counterparts.

Of the several techniques available, DEXA has become the most widely used technique for measuring BMD because of its low radiation, availability, capacity to evaluate multiple sites, and ease of use (Genant, et al., Am J. Med. 91(suppl5B): 49S-53S (1991)). Dual energy x-ray absorptiometry can measure soft-tissue composition (lean and fat mass) and bone mass or bone density at the lumbar spine, hip, and forearm, as well as total-body BMD, with greater precision and faster scanning times than the dual-photon absortiometry (Consensus Development Center: "Prophylaxis and treatment of osteoporosis" in Am J Med. 90:107-101(1991)). As a screening procedure, DEXA is limited by its relatively high equipment cost. The accuracy of this technique has not been fully documented for measuring of all skeletal sites.

A standard bone mineral report consists of measurements expressed as bone mineral content (the amount of hydroxyapatite, in grams)and converted to area density (grams per square centimeter) within the region of interest. In addition, normal values are provided according to sex and race and are plotted according to age. Demographic data, including the clinical indications and the patient's age, sex, race, weight, and height, are also considered. To interpret a standard bone mineral report, a region of interest must be selected. To compare individuals, the sites of measurement should be constant because the bone mineral content varies between different bones and between different regions of the same bone. The results are compared with normative values, and standard curves of normative values are provided for individuals of both sexes and several races. Comparison of measured values with mean values for normal young or age-matched individuals permits an assessment of the risk of fracture.

The World Health Organization recently attempted to clarify definitions and to assist clinicians in their interpretation of bone densitometry results. According to that report, a normal value for bone mineral content is within 1 standard deviation (SD) of the mean value for young adults of the same age and sex (that is, the t score is more than −1). Osteopenia is considered to be present when the value for bone mineral content is more than 1 SD but not more than 2.5 SDS below the mean for young adults (that is, the t score is less than −1 and more than −2.5). Osteoporosis is considered to be present when the value is more than 2.5 SDS below the mean bone mineral content for young adults (that is, the t score is less than −2.5) (Kanis et al., 1994). Severe osteoporosis is considered to be present when the value for bone mineral content is more than 2.5 SDS below the mean for young adults and there is at least one so-called fragility fracture (assumed to be associated with osteoporosis because it occurred as a result of slight trauma). Generally, the t score is used for the diagnosis of low bone mass or osteoporosis.

Physicians should initiate therapy to reduce the patient's risk of fracture on the basis of the presence or absence of risk factors for osteoporosis. Therapy should be initiated to reduce the risk of fracture in women who have a bone mineral density t score of less than −2 in the absence of risk factors and in those who have a t score of less than −1.5 if other risk factors are present.

B. Biochemical Markers of Bone Turnover

A combination of markers of bone turnover can be used in a variety of ways in the clinical investigation of osteoporosis. Growing evidence suggests that the rate of postmenopausal bone loss may be determined by biochemical markers, such that a single biochemical assessment shortly after menopause, in conjunction with a bone mass measurement, may be used to identify women with high bone turnover and who are therefore likely to sustain a high rate of bone loss. In osteoporotic patients, markers may be used to identify the subgroup of patients with high bone turnover who may benefit from a different therapeutic strategy from that used in patients with low bone turnover. Finally, markers can be used in the clinical investigation of new therapeutic agents to monitor their effect and mechanism of action (Consensus Development Center 1991).

Osteocalcin is a bone-specific protein secreted by osteoblasts, the bone-forming cells, and its serum level is a sensitive marker of the rate of bone formation. Other markers of bone formation include serum levels of total and bone-specific alkaline phosphatase and serum type 1 collagen propeptide. Pyridinoline and deoxypyridinoline are collagen crosslinks that are released into the blood and urine during the degeneration of type 1 collagen in the process of osteoclastic bone resorption (Delmes "Clinical use of biochemical markers of bone remodeling in osteoporosis," in Osteoporosis Christiansen, et al., (eds). Copenhagen, Osteopress, pp 450-458 1990). Urinary excretion of pyridinoline such as hydroxylysylpyridinoline and lysylpyridinoline has been shown to be a more sensitive and specific marker of bone resorption than conventional markers such as urinary hydroxyproline (Uebelhart, et al., Bone Mineral, 8, 87-96 (1990)). Plasma tartrate-resistant acid phosphatase is another marker of bone resorption (Delmes, (1990)).

C. Radiographic Findings

A reduction in bone calcium content must exceed 30% to be observed with certainty on conventional radiographs. Radiographically evident thinning of the cortices of long bones or vertebral bodies may be noted. Plain radiographs are generally inaccurate in the diagnosis of osteoporosis as the demonstration of bone density is strongly dependent on radiographic technique.

III. Identification of Bacterial or Viral Markers for Osteoporosis

A. Bacterial Markers for Osteoporosis

Bacterial Infections and Bone Pathology

There is a range of bacteria involved in bone pathology. The key question to be addressed in these diseases is how the bacteria stimulate pathology and how they get into bone in the frost place. In infections of the appendicular and axial skeleton, the answer may lie in bacteria expressing receptors for bone matrix components. For example, *Staphylococcus aureus* contains receptors for fibronectin (Raja, et al., Infect. Immun., 582593-2598 (1990); laminin (Mota, et al., Infect. Immun., 56,1580-1584 (1988)), collagen (Patti, et al., Infect. Immun. 62:152-161 (1994)), and bone sialoglycoprotein (Ryden, et al., Eur. J Biochem. 184:33 1-336 (1989)) that presumably serve to trap blood-borne organisms in bone. As bacteria do not invade the periodontal tissues, the accepted paradigm is that local pathology is due to the release of soluble bacterial virulence factors (Wilson, Sci. Prog. 78:19-34 (1995)) and that this could be a general mechanism in all bone infections.

TABLE 1

Bacteria Involved in Pathological Bone Remodeling

| Disease | Organism |
|---|---|
| Periodontitis (Schluger et al., 1990) | *Actinobacillus actinomycetemcomitans* *Porphyromonas gingivallis* *Eikenella corrodens* *Fusobacterium nucleatum* *Prevotella inter-media* *Campylobacter rectus.* |
| Osteomyelitis (Jaffe, 1972; Schmid, 1993) | *Staphylococcus aureus* *Staphylococcus epidermidis* Salmonella spp. *Escherichia coli*, etc. |
| Bacterial arthritis (Ho, 1993; Livneh et al., 1983) | *Staphylococcus aureus* *Neisseria gonorrhoea* *Neisseria meningitis* *Mycobacterial tuberculosis* *Haemophius infruenzae* *Pasteurella multocida*, etc. |
| Infected metal implants (Ross, 1991) | *Staphylococcus aureus* *Staphylococcus epidermidis* |

Three possibilities exist of how bacteria cause pathological bone loss: (a) bacteria directly destroy the noncellular components of bone by liberating acid and proteases, (b) bacteria promote cellular processes that stimulate the degradation of bone, or (c) bacteria inhibit the synthesis of bone matrix. Mechanisms (b) and (c) may be either a direct effect of components released by bacteria or a consequence of the induction of host factors, for example, cytokines or prostaglandins that then act on bone cells. Mechanisms implicated in the pathology of dental caries are likely to be only a minor mechanism in skeletal bone pathology.

The Capacity of Bacteria and their Products to Inhibit Bone Formation

In addition to stimulating in vitro bone resorption, endotoxin-LPS has also been reported to inhibit bone collagen and noncoliagenous protein synthesis (Millar, et al., Infect. Immun., 57,302-306 (1986)). A number of reports have suggested that extracts of dental plaque or of cultured periodontopathic bacteria can inhibit bone matrix synthesis (Hopps, et al., Periodontal disease: pathogens and host immune response. Hamada, et al., eds., (Quintessence Publishing Co., Ltd., Tokyo) pp. 307-320 (1991); Multanen, et al., J. Clin. Periodontol. 1:729-739 (1985)). Surface-associated proteins from oral bacteria are also able to inhibit bone matrix synthesis (Meghji, et al., J. Periodontol. 63:736-742 (1992)).

Certain periodontopathic bacteria produce factors that have general antiproliferative activity (Helgeland and Nordby, 1993; Kamen 1981; Kataoka et al., 1993; Larjava et al., 1987; Meghji, et al., Arch. Oral Biol., 37:637-644 (1992); Saito et al., 1993; Shenker et al., 1991). These could possibly play a role in inhibiting osteoblast proliferation and thus impair bone remodeling. These various biological activities have not been purified or characterized. An antiproliferative protein from A. *actinomycetemcomitans* that is most active against human osteoblast-like cell lines suggests some specificity for bone. This 8-kDa protein (White et al., 1995), "termed gapstatin," does not inhibit DNA synthesis directly but inhibits cell cycle progression by blocking cells in the G2 phase of the cell cycle. Kinetic studies of synchronized cell populations reveal that gapstatin acts only on cells in S phase. This molecule may act by inhibiting the synthesis of cyclin BI, a protein required to ensure that cells make the transition from G2 to mitosis. As bone remodeling and matrix synthesis require the continued production of osteoblasts and osteoclasts, the action of gapstatin could inhibit new bone matrix formation. Such an effect would be particularly damaging if it were to occur in concert with molecules stimulating bone breakdown, such as cpn60. It is possible that gapstatin could inhibit the formation of osteoclasts.

*Bordetella bronchiseptica* produces a 145 kDa dermonecrotic toxin DNT) that is responsible for turbinate atrophy in swine atrophic rhinitis (Ackerman et al., 1991; Dunan et al., 1966). Histologically, the lesions induced by *B. bronchiseptica* suggest impaired osteoblastic function (Silveira et al., 1982). There is one report of the effect of DNT on cultured bone, and its effects were not particularly striking (Kiman et al., 1987). However, when added to the murine osteoblastic cell line MC3T3-El, it caused changes in cellular architecture and potently inhibited (50% inhibitory concentration, 100 pg/ml)the osteoblasts' capacity to produce both alkaline phosphatase and collagen (Horiguchi et al., 1991), an action that could seriously affect bone remodeling if replicated in vivo. It has recently been reported that DNT is a potent stimulator of tritiated thymidine incorporation into MC3T3-El cells with a 50% effective dose of approximately 1 ng/ml. In spite of this incorporation of label, the numbers of MC3T3-El cells in culture did not increase. The major consequence of exposure to DNT was the appearance of multinucleated osteoblasts. Another cell cycle-inhibitory protein has recently been isolated from the periodontopathic bacterium *Fusobacterium nucleutum*. This protein blocks human T lymphocytes in the mid-$G_1$ phase of the cell cycle (Shenke and Datar, 1995). It is expected to stimulate bone resorption.

It is now becoming clear that bacteria produce a range of proteins that are able to interfere with the mammalian cell cycle. One can suggest that the activity of these proteins represents a new bacterial virulence mechanism. The importance of the proliferation and maturation of bone cell lineages in bone remodeling is presumably the reason that the bacterial cell cycle modulatory proteins discovered to date induce bone pathology or come predominantly from bacteria implicated in diseases involving bone matrix loss.

B. Molecular Chaperone Markers for Osteoporosis

Molecular chaperones, also known as heat shock proteins (hsp), are essential to prokaryotic and eukaryotic cellular organisms through their chaperone function during the intracellular (un)folding, assembly and translocation of proteins. Four main families of structurally related hsps are distinguished based on their molecular weights: Hsp90, Hsp70, Hsp60 and small Hsps. By definition, Hsp expression is elevated in cells undergoing stress, such as those in damaged or inflamed tissue. Conditions as diverse as a rise in temperature, hypoxia, irradiation, infection and exposure to toxic chemicals can all result in increased Hsp expression. Within the Hsp families, individual members have a unique degree of sequence homology. For Hsp60, the human protein has 50% sequence identity with the mycobacterial homologue, with a further 20% conservative substitutions, causing several areas in the human molecule to be fully identical to the bacterial protein.

The best studied molecular chaperones are the chaperonins (cpns) which consist of two interacting oligomeric proteins known as cpn10 and cpn60 (from the molecular masses of their subunits). The cpns form heptameric structures with protein folding occurring within the cavity of the cpn60 oligomer, a process requiring heptameric cpn10. In contrast, the Hsp70 family of molecular chaperones act as monomers. The Hsp90 family is one of the most abundant proteins in unstressed eukaryotic cells and this dimeric protein interacts with a large number of intracellular proteins, most notably the steroid receptors. There are also a number of lower molecular mass molecular chaperones (Wilson, et al., J. Periodontal. Res. 20:484-491 (1985)). A number of other less well characterized molecular chaperones are known. Hsp47 is known to be a collagen molecular chaperone (Laemmli, 1970). Certain of the molecular chaperones cpn60, Hsp70, and Hsp104, bind and hydrolyze adenosine triphosphate.

To isolate and further analyze HSP of a mammalian subject, tissues or cells are generally sampled under conditions which do not elevate HSP levels. The method of tissue or cell sampling, HSP isolation and measurement, and formation of HSP complexes are described by U.S. Pat. Nos. 5,232,833 and 5,780,246 to Sanders, incorporated herein by reference.

Collection of human bone samples from representative age groups and characterization of the sample pool with respect to measuring bone density Representative bone samples can be obtained from a qualified bone bank. The sample pool is then characterized to generate a database based on measurements of bone density. Many bone density techniques have shown clinical utility for assessing fracture risk. Presently, there are more than 20 different devices available for measurement of bone density. Some devices offer advantages in terms of versatility (i. e., the number of skeletal sites that can be measured), ability to monitor response, cost, availability, and ease of use (Table 2). Currently, no single device exists that ideally addresses all of these clinical requirements.

TABLE 2

Comparison of Bone Densitometry Techniques

| Method[a] | Clinical utility | Versatility | Ease of use | Availability | Cost | Radiation dose |
|---|---|---|---|---|---|---|
| SXA | + | − | + | + | + | + |
| DXA | ++ | ++ | + | + | − | + |
| pDXA | + | − | + | + | + | + |
| QCT | ++ | − | − | + | − | − |
| pQCT | + | − | + | − | − | + |
| QUS | + | − | + | + | + | ++ |

[a]SXA, single X-ray absorptiometry; DXA, dual X-ray absorptiometry; pDXA, peripheral dual X-ray absorptiometry; QCT, quantitative computed tomography; pQCT, peripheral quantitative computed tomography; QUS, quantitative ultrasonography.

C. Confirmation of Osteoporosis According to the WHO

For bone mineral density (BMD) measurements to be clinically useful, they need to be expressed in comparison to established normative data. All BMD manufacturers provide normative databases for this purpose. These databases are derived from bone density measurements of large groups of both men and women of different ages and races. Comparisons are expressed as percentage of or as the number of standard deviations from the age-matched and young normal values for healthy individuals of the same age, sex, and race.

Percentage scores are determined with respect to either the age-matched normal BMD (AMN) or the young normal BMD (YN) using the following equations:

Percent of age matched=$[1+(BMD-AMN/AMN)] \times 100\%$ (Harris, et al., Bone Miner. 17:87-95 (1992))

Percent of young normal=$[1+(BMD-YN/YN)] \times 100\%$ (Faulkner, et al., J. Bone Miner Res. 11(Suppl 1):S96 (1996))

Typically, the densitometry analysis software can calculate these percentage values. The standard deviation (SD) scores are also usually provided by the densitometry software. The age-matched SD score is commonly referred to as the "Z-score," whereas the young normal standard deviation score has been labeled the "T-score." However, different densitometry systems may have different names for these parameters.

The age-matched or Z-score is calculated as the difference between the patient's BMD and the normal BMD for those of the same age, sex, and race (AMN), divided by the SD of the normal population. This is calculated by the densitometry system using the following equation:

$Z=(BMD-AMN)/SD$

The young normal or T-score is defined in a similar fashion, except the BMD difference is expressed in terms of the YN bone density:

$T=(BMD-YN)/SD$

For the diagnosis of osteoporosis, the WHO has defined the following criteria for the assessment of osteoporosis based on a BMD measurement at any skeletal site.
 1. Normal: A BMD not more than 1 SD below YN (T-score=/<−1).
 2. Low bone mass (osteopenia): A BMD between 1 and 2.5 SD below YN (T-score<−1 and >−2.5).

3. Osteoporosis: A BMD 2.5 or more SD below YN (T-score =/<−2.5).
4. Severe osteoporosis: A BMD 2.5 or more SD below young normal (T=/<−2.5) and the presence of one or more fragility fractures.

Sample analysis to identify presence of various bacterial and mammalian chaperons in bone samples.

Extraction of Chaperone Molecules from Bone Samples

All bone samples (BS) can be harvested in sterile saline, centrifuged, washed briefly in saline, and lyophilized. Chaperone molecules are removed from the various bacteria by, for example, by gentle saline extraction as described by Wilson et al., (1985). Briefly, bone samples are suspended in sterile saline and stirred gently at 4° C. for 1 h. The debris is then removed by a means such as centrifugation and the soluble components are dialyzed extensively against distilled water and lyophilized. The protein content of the BS can be determined by a method such as described by Lowry, et al., J. Biol. Chem. 193:265-275 (1951), the carbohydrate content can be determined by a method such as described by Dubois, et al., Anal. Chem. 28:350-356 (1956), and the nucleic acid content by absorption at 260/280 run. The LPS content can be measured using a commercial chromogenic Limulus amebocyte lysate assay, such as one market by Pyrogent, Byk-Mallinckrodt, London, UK, according to the manufacturer's instructions.

SDS-PAGE

The components of the BS can be analyzed by for example SDS-PAGE using 12% gels according to a method such as one described by Laemmli, et al., Nature (Lond.) 227:680-685 (1970). One of ordinary skill in the art will recognize other suitable methods. Samples can be diluted to an appropriate extent such as 1:1 with sample buffer and boiled for a period such as 5 min. before loading. Gels can be run using for example a MiniProtean II system (Bio Rad Laboratories) and stained with for example Coomassie brilliant blue (Sigma Immunochemicals). The molecular weight markers can be based on Dalton standards (Sigma Immunochemicals) or any other standards which one of ordinary skill in the art can recognize. Gels can also be silver stained using a commercial kit such as one marketed by Gelcodeo mark silver stain kit; Pierce, Rockford, Ill., to detect both the presence of protein and carbohydrate.

Two-dimensional PAGE

Two-dimensional PAGE gels can be run using a method such as one described by O'Farrell, et al., J. Biol. Chem. 250:4007-4021 (1975). Gels can be run using for example a MiniProtean™ II system and stained with, for example, Coomassie blue, with similar molecular weight markers as above. The first dimension, isoelectric focusing, can be over a pH range of 1-14, preferably 3-10. Second dimension separation can be carried out by, for example, molecular mass separation using a 12%SDS-PAGE gel.

Immunoblotting

Samples separated on one-or two-dimensional SDS-PAGE can be electroblotted onto membranes such as hnmobilon P polyvinyldifluoride membranes marketed by Millipore Corp., Bedford, Mass. overnight (Laemmli, 1970). Membranes can be washed with, for example, PBS containing 0.1% Triton X-100 (Sigma Immunochemicals)(PBS-T) and blocked with PBS-T containing 2% FCS (blocking buffer) (SeraLab). Blocked membranes can then be incubated with the test antibody (in blocking buffer) for a period such as 1 h and washed with buffer, for example, PBS-T. Bound test-antibody (anti-mouse) IgG can be detected using for example peroxidase labeled goat anti-mouse IgG (gamma-chain specific) (Sigma Immunochemicals) at 1:1,000 in PBS-T2% FCS. After a final wash, the blots can be developed with a solution such as 1 mg/ml 3,3 prime-diaminobenzidine tetrahydrochloride (Sigma Immunochemicals) in 50 mM Tris (Sigma Immunochemicals), pH 7.6, containing 150 mM NaCl (BDI-I) and 0.05% hydrogen peroxide (Sigma Immunochemicals). Each reaction can be terminated by extensive rinsing with distilled water.

Protein Purification

Crude BS can be fractionated using column chromatography such as fractionation at 4° C. on a Q-Sepharose™ anion exchange column (50 cm times 1.6 cm). The column can be equilibrated in a solution such as 20 mM Tris-HCl, pH 8.5 (buffer A). The BS (generally 100-400 mg) can be loaded on in the same buffer. The column can be washed with a solution such as 500 ml of buffer A and then eluted with for example 1,000 ml linear gradient of O-2 M NaCl in buffer A. Fractions can be collected, whose absorbance can be monitored at 280 nm. The location of the osteolytic chaperone protein can be determined by a combination of activity assay, for example, SDS-PAGE, and the Western blot analysis. Fractions containing osteolytic activity can be dialyzed against for example deionized water to remove salt and lyophilized. The fraction with the highest specific activity and the least number of protein bands on SDS-PAGE can then be further fractionated at room temperature on a second column such as an anion exchange column.

The purity of the fractions can again be assessed, visually by SDS-PAGE or using another means recognizable by one of ordinary skill in the art, and 100 pg of the cleanest fraction can be dialyzed against 50 mM of Tris but&, pH 7.6, containing 10 mM KCl and 10 mM MgCl2 (buffer C). This sample can be run on for example a 5-ml ATP-Sepharose™ (Sigma Immunochemicals) column. The column can be washed with buffer C and bound protein eluted in 5 mM ATP (Sigma Immunochemicals), also in buffer C. Protein can be located by SDS-PAGE and visualized using a silver stain kit (Sigma Immunochemicals). Gel filtration can be used to determine the molecular mass range of the osteolytic chaperone protein isolated by a method such as ATP-affinity chromatography. This can be achieved by running the purified protein on a column such as Bio-Sil TSK250 (Bio Rad Laboratories) column in a buffer such as 0.1 M sodium phosphate buffer, pH 6.7, and measuring the absorption of the collected fractions at a wavelength in the range between 205 and 280 nm.

Data analysis and correlation to clinical outcome variables

The experimental findings and clinical bone densitometry and Q-CT measurements can be documented using, for example, a standardized relational computer database using a numerical code system. In one embodiment, the computer program SPSS/PC+9.0 (SPSS Inc., 44 N. Michigan Ave., Chicago, Ill. 60611) is used for statistical analysis of the compiled data. Descriptive statistics of the raw data can be carried out using frequency tables. Normal distribution can be determined by fitting to normality and by obtaining normal probability plots, where the ranked observed residuals (deviation from the mean) are plotted on the x-axis against the standardized values of the normal distribution on the y-axis. Normal distribution can then be indicated if the observed residuals fall onto the straight line. Significant differences between means can be evaluated using a T-test for dependent and independent samples and one-way ANOVA analysis of variance. In case of a statistically significant F-Test from an ANOVA using multivariate variables, the contributing means can be differentiated by post-hoc comparison using a Tukey HSD test for unequal samples sizes. The latter two tests can determine the occurrence of the various Chaperone Molecules and the presence of an osteopenic bone sample according to a patient's age and gender and other concomitant medical conditions. The predominant chaperone molecule correlating with osteopenia can thus be identified.

The relationships between osteopenia, age, gender, other contributing factors, and the presence of chaperone molecules can be established using, for example, a cross tabulation method by generating multiple-way frequency tables. For each possible combination of these variables, these tables yield a cell frequency, i.e. the number of cases in the patient population that had this particular combination. In addition, such a cross tabulation method allows to evaluate the reliability of the test of these relationships. Hence, the presence of osteopenia, age, gender, other contributing factors such as medical conditions are categorical variables. Multiple simultaneous relations and interactions between the variables of the multipleway frequency table can be examined on the basis of log-linear equations, which allow computation of the cell frequencies that would have been expected if the variables involved were unrelated. This can be performed using for example an iterative proportional fitting procedure. Thus, significant deviations of the observed from the expected frequencies can reflect a statistically significant relationship between a specific chaperone molecule and osteopenia. Significance testing of deviations of the observed from the expected frequencies can be performed via a Pearson Chi-square test. The residual frequencies can be calculated by subtracting the expected frequencies from the observed frequencies. If no relationship exists, all residual frequencies are expected to consist of positive and negative values of similar magnitude and to be evenly distributed across the cells of the frequency table. Plotting the residuals is therefore used as another means of assessing correlations between the presence of chaperone molecules with osteopenia. In all statistical tests employed in this study, a significance level such as one of $p < 0.05$ can be chosen. One of ordinary skill in the art can choose a proper significance level.

IV. Diagnosing Osteoporosis using Bacterial and/or Molecular Chaperon Markers

The method of diagnosing osteoporosis disclosed herein generally includes 1) sampling the tissue or cells of a mammalian subject, 2) measuring the level of a marker and 3) designating the mammalian subject as having osteoporosis if the level of the marker is higher than a standard level of the marker in a member of a control group. The method may optionally include a step of isolating the marker. The control group is selected according to factors such as geographical location, gender and/or age. Alternatively, two or more measurements of the marker in the same mammalian subject are made and compared during a course ranging from several hours for example 6 hours, several days for example 10 days, to several months or several years. If the level of the marker of the latter measurement or assay is higher than the level of the marker in the previous measurement or assay, the mammalian subject is designated as having osteoporosis. Sometimes, when desirable, the two method of diagnosing osteoporosis can be used in combination.

Preferably, the mammalian subject is a human being. Most preferably, the mammalian subject is a postmenopausal female.

The marker can be either a bacteria, a bacteria produced factor, or a chaperon molecule. In one embodiment, the marker is a bacteria. Representative bacterial markers are: *Actinobacillus actinomycetemcomitans, Porphyromonas gingivallis, Eikenella corrodens, Fusobacterium nucleatum, Prevotella inter-media, Campylobacter rectus, Staphylococcus aureus, Staphylococcus epidermidis, Salmonella* spp., *Escherichia coli, Neisseria gonorrhoea, Neisseria meningitis, Mycobacterial tuberculosis, Haemophius infruenzae, Pasteurella multocida.*

In another embodiment, the marker can be a chaperon molecule. Representative chaperon molecular markers are: HSP 70, HSP 70, gp 96, cpn10, and cpn20, alone or in combination. Preferably, the marker is a human HSP.

In still another embodiment, the marker can be a bacteria produced factor such as endotoxin-LPS, gapstatin, or dermonecrotic toxin (DNT).

V. Methods of Treating or Preventing Osteoporosis

A. Preparation and Purification of HSP Reagents

Preparation and purification of HSP proteins and their respective peptide complexes are within the knowledge in the art. The complexes can be intracellularly produced complexes having HSPs from a selected recombinant host cell and antigenic peptides expressed from cDNAs of a diseased bone or tissue cell; the antigenic peptides of the complex are thus representative of antigenic peptides found in such bone cell. Generally, the methods of preparing HSP complexes include the steps of obtaining (e.g., isolating) diseased bone or other tissue cells from one or more individuals, preparing RNA from the cells, making cDNA from the RNA, introducing the cDNA into host cells, culturing the host cells so that the diseased bone cell-derived cDNAs are expressed, and purifying HSPs-peptide complexes from the host cells.

The cDNA prepared from disease bone or tissue cell RNA, herein referred to as "diseased bone cDNA", is optionally amplified prior to introduction into a host cell for expression. The cDNAs are optionally inserted into a cloning vector for replication purposes prior to expression. The cDNAs are inserted into an expression vector or intrachromosomally integrated, operatively linked to regulatory element(s) such as a promoter, for purposes of expressing the encoded proteins in suitable host cells in vitro. The cDNAs are introduced into host cells where they are expressed by the host cells, thereby producing intracellularly noncovalent complexes of HSPs and peptides. The recombinant host cells can be cultured on a large scale for production of large amounts of the immunogenic complexes. The diseased bone cDNA library can be stored for future use (e.g., by lyophilization or freezing), or expanded by replication in a cloning vector in suitable host cells to meet increased demand for the immunogenic complexes.

The immunogenic compositions prepared from the host cells expressing the diseased bone cDNAs comprise complexes of HSPs of the host cell noncovalently associated with peptides, inter alia, those derived from the diseased bone cells from which the RNA was originally derived. Such complexes can induce an immune response in a patient against the diseased bone cells that is therapeutically or prophylactically efficacious. Preferably, the patient is the subject from whom the diseased bone cells used to make cDNA were obtained. Alternatively, the diseased bone cells can be from one or more subjects different from the patient but having diseased bone of the same tissue type.

Optionally, host cells for expression of the diseased bone cDNAs can also be genetically engineered to coexpress recombinantly one or more HSP genes so that increased amounts of complexes comprising immunogenic peptides noncovalently associated with a HSP can be produced.

The preparation and purification of HSP proteins, their respective peptide complexes, and isolation of antigenic/immunogenic components are disclosed in U.S. Pat. Nos. 5,830,464; 5,948,646; and 6,030,618 to Srivastava ("the Srivastava patents"). The Srivastava patents also described the in vitro production of HSP-antigenic molecule complexes and the proper procedure for determination of immunogenicity of HSP-peptide complexes. The Srivastava patents, and the references included therein, are incorporated by reference herein.

In a preferred embodiment, the HSP-antigenic molecule complex is autologous to the individual; that is, the complex is isolated from either the infected cells of the individual himself (e.g., preferably prepared from infected tissues of the patient). Alternatively, the complex is produced in vitro (e.g., wherein a complex with an exogenous antigenic molecule is desired). Alternatively, the HSP and/or the antigenic molecule can be isolated from the individual or from others or made by recombinant production methods using a cloned HSP originally derived from the individual or from others. Exogenous antigens and fragments and derivatives (both peptide and non-peptide) thereof for use in complexing with HSPs, can be selected from among those known in the art, as well as those readily identified by standard immunoassays known in the art by the ability to bind antibody or major histocompatibility molecules (MHC molecules) (antigenicity) or generate immune response (immunogenicity). Complexes of HSPs and antigenic molecules can be isolated from infected tissue of a patient, or can be produced in vitro (as is necessary in the embodiment in which an exogenous antigen is used as the antigenic molecule). The HSP-antigenic molecule complex that is administered to the patient can be the same or different from the HSP-antigenic molecule complex used to sensitize the APC that are administered to the patient. In a specific embodiment wherein the APC and complexes are administered concurrently, the APC and purified HSP-antigenic molecule complexes can be present in a single composition, or different compositions, for administration.

HSPs that can be used include but are not limited to, HSP 70, HSP 70, gp 96, cpn10, and cpn20, alone or in combination. Preferably, the HSPs are human HSPs. Although the HSPs can be allogeneic to the patient, in a preferred embodiment, the HSPs are autologous to (derived from) the patient to whom they are administered. The HSPs and/or antigenic molecules can be purified from natural sources, chemically synthesized, or recombinantly produced.

The immunogenic HSP-peptide complexes disclosed herein may include any complex containing an HSP and a peptide that is capable of inducing an immune response in a mammal. The peptides are preferably noncovalently associated with the HSP. Preferred complexes may include, but are not limited to, HSP 60-peptide, HSP 70-peptide and HSP 70-peptide complexes. For example, an HSP called gp 96 which is present in the endoplasmic reticulum of eukaryotic cells and is related to the cytoplasmic HSP 70s can be used to generate an effective vaccine containing a gp 96-peptide complex.

The compositions comprising HSP noncovalently bound to antigenic molecules can be administered to elicit an effective specific immune response to the complexed antigenic molecules (and not to the HSP). The HSP-antigenic molecule complexes are preferably purified to at least 70%, 80% or 90% of the total mg protein. In another embodiment, the HSP-antigenic molecule complexes are purified to apparent homogeneity, as assayed by sodium dodecyl sulfate-polyacrylamide gel electrophoresis.

Immunogenic or antigenic peptides that are endogenously complexed to HSPs or MHC antigens can be used as antigenic molecules for treating and/or preventing bone diseases. For example, such peptides may be prepared that stimulate cytotoxic T cell responses against different viral proteins including, but not limited to, proteins of immunodeficiency virus type I (HIV-I), human immunodeficiency virus type II (HIV-II), hepatitis type A, hepatitis type B, hepatitis type C, influenza, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus and polio virus.

In another embodiment the HSP-antigenic molecule complex to be used is a complex that is produced in vivo in cells. Alternatively, in an embodiment wherein one wishes to use antigenic molecules by complexing them to HSPs in vitro, HSPs can be purified for such use from the endogenous HSP-peptide complexes in the presence of ATP or low pH (or chemically synthesized or recombinantly produced). The procedures for purification of HSPs and their respective complexes are described in the Srivastava patents. The protocols described herein may be used to isolate HSP-peptide complexes, or the HSPs alone, from any eukaryotic cells for example, tissues, isolated cells, or immortalized eukaryote cell lines infected with a preselected intracellular pathogen.

B. Exogenous Antigenic Molecules

Exogenous antigens or antigenic portions can be selected for use as antigenic molecules, for complexing to HSPs, from among those known in the art or determined by immunoassay to be able to bind to antibody or MHC molecules (antigenicity) or generate immune response (immunogenicity). To determine immunogenicity or antigenicity by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radio-isotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are envisioned for use. In one embodiment for detecting immunogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby, 1985, Summary, in Vaccines 85, Lerner, et al. (eds.), Cold Spring Harbor Laboratory, Cold Spring Harbor, N.Y., pp. 388-389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen. Preferably, where it is desired to treat or prevent osteoporosis caused by viral infections of bone, molecules comprising epitopes of known viruses are used, as discussed above. Preferably, where it is desired to treat or prevent osteoporosis caused by bacterial infections of bone, molecules comprising epitopes of known bacteria are used, as discussed above. Where it is desired to treat or prevent osteoporosis caused by protozoal infections of bone, molecules comprising epitopes of known protozoa are used. For example, such antigenic epitopes may be prepared from protozoa including, but not limited to, leishmania, kokzidioa, and trypanosoma. Where it is desired to treat or prevent osteoporosis caused by parasitic infections of bone, molecules comprising epitopes of known parasites are used. For example, such antigenic epitopes may be from parasites including, but not limited to, chlamydia and rickettsia.

C. Method of Treating Osteoporosis

Osteoporosis caused by infectious diseases of bone that can be diagnosed using a chaperon molecule marker can be caused by bone infectious agents including, but not limited to, viruses, bacteria, fungi, protozoa and parasites, as discussed above. The method of treating osteoporosis disclosed herein generally includes administering to a mammalian subject a drug composition effective to treat the infectious agent causing the osteoporosis. The drug composition generally contains a drug and optionally a drug delivery carrier and/or one or more biocompatible excipients. Exemplary drug delivery carriers are liposomes, micro or nanoparticles formed of natural or biodegradable synthetic polymers such as polylactic acid, polyglycolic acid, polyhydroxyalkanoates, natural or chemically modified starches, chitosan, and proteins such as gelatin. In the case wherein the marker for osteoporosis is a chaperon molecule such as a HSP, the drug composition can include one or more complexes formed of the HSP with another molecule.

The therapeutic reagents can be essentially the same as the diagnostic reagents, purified and prepared according to GMP standards. Modes of administration include but are not limited to subcutaneously, intramuscularly, intravenously, intraperitoneally, intradermally or mucosally.

The therapeutic regimens and pharmaceutical compositions disclosed herein may be used with additional immune response enhancers or biological response modifiers including, but not limited to, the cytokines IFN-.alpha., IFN-.gamma., IL-2, IL-4, IL-6, TNF, or other cytokine affecting immune cells. The complexes of the HSP and antigenic molecule are administered in combination therapy with one or more of these cytokines.

Drug solubility and the site of absorption are factors which should be considered when choosing the route of administration of a therapeutic agent. In an embodiment, HSP-antigenic molecule complexes may be administered using any desired route of administration. Advantages of intradermal or mucosal administration include use of lower doses and rapid absorption, respectively. Advantages of subcutaneous or intramuscular administration include suitability for some insoluble suspensions and oily suspensions, respectively. Mucosal routes of administration include, but are not limited to, oral, rectal and nasal administration. Preparations for mucosal administrations are suitable in various formulations as described below.

If the complex is water-soluble, then it may be formulated in an appropriate buffer, for example, phosphate buffered saline or other physiologically compatible solutions, preferably sterile. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, or rectal administration.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

For administration by inhalation, the compounds for use can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

D. Resistance To Osteoporosis Induced by Bacteria or HSPs

Osteoporosis caused by bacterial infection or bone diseases can be treated by immunizing by administering to a mammalian subject an immunogenic composition. In one embodiment, the immunogenic composition may comprise an attenuated or modified infectious agent. In another embodiment, the immunogenic composition may include a HSP. Immunization to bone diseases by HSPs are well documented. For example, in rat adjuvant arthritis (AA), resistance could be induced by immunization with mycobacterial HSP 60 in incomplete Freund's adjuvant (IFA). Similar findings were obtained with mycobacterial and Escherichia coli HSP 70 and HSP10, and DNA vaccination with mycobacterial HSP 60 was also protective. Bardwell, J. C. A., et al., Proc. Natl. Acad. Sci. USA, 81:848-852 (1984); Greenberg, S. G., J. Neuroscience, 5:1239-45. Immunization with a recombinant vaccinia virus expressing either mycobacterial or human HSP 60 was found to suppress AA, even when administered after disease induction. For mycobacterial HSP 60, oral administration was also shown to inhibit rat AA; in this case, there was evidence for the induction of transforming growth factor (TGF-beta)-producing cells that suppressed proliferative responses to the disease eliciting mycobacterial antigen from Mycobacterium tuberculosis (Mt), thus pointing to a potential mechanism of disease resistance. Irby, R. B. et al.

TABLE 3

HSPs and protection in autoimmune disease models*

| Model | Animal[a] | HSPs | Route | Effect |
| --- | --- | --- | --- | --- |
| Adjuvant arthritis | R | MtHSP 60, HSP 70, HSP 10 | Subcutaneous | Prevention |
| Streptococcal cell wall arthritis | R | MtHSP 60 | Subcutaneous | Prevention |
| Avridine arthritis | R | MtHSP 60, HSP 70 | Subcutaneous | Prevention |
| Adjuvant arthritis | R | MtHSP 60 | Vaccinia | Treatment |
| Adjuvant arthritis | R | HumHSP 60 | Vaccinia | Treatment |
| Adjuvant arthritis | R | MtHSP 60 | Oral | Prevention |
| Adjuvant arthritis | R | M1HSP 60 | Naked DNA | Prevention |
| NOD diabetes | M | MtHSP 60 | Subcutaneous | Prevention |
| NOD diabetes | M | HumHSP 60 peptide | Subcutaneous | Prevention, treatment |
| Pristane arthritis | M | MtHSP 60 | Subcutaneous | Prevention |
| Collagen arthritis | M | MtHSP 60 | Subcutaneous | Prevention |
| Collagen arthritis | R | MtHSP 70 | Subcutaneous | Partial prevention |
| Yersinia arthritis | R | Mtsp 60 | Subcutaneous | Prevention |
| EAE | R | MtHSP 60 peptide | Subcutaneous | Prevention |

Preimmunization using HSP 60 has been found to induce resistance to autoimmunity in other arthritis models, such as streptococcal cell-wall-induced arthritis-8 and, importantly, nonmicrobially induced models such as avridine-9 (a synthetic nonimmunogenic lipoidal amine) or pristane-induced arthritis, as well as collagen-induced arthritis. Similarly, development of experimental autoimmune encephalomyelitis (EAE) in rats and diabetes in nonobese diabetic (NOD) mice has been found to be inhibited by prior immunization with HSP 60. Therefore, immunologic exposure to HSPs could lead to resistance against various forms of induced or spontaneous autoimmunity.

The reports on the basis of the various models collectively indicate that resistance to autoimmunity induced by HSP 60 operates irrespective of the actual autoimmune disease trigger and that the suppressive effect is due to the induction of anti-inflammatory T cells responding to stress- (inflammation) upregulated self-HSP. The upregulated expression of self-HSP 60 in the inflamed joints has been shown both in the experimental models and in humans. HSP 60-mediated protection is documented in NOD diabetes, and upregulated expression of self-HSP occurs in inflamed islets, thus it seems that self-HSP-specific anti-inflammatory T cells can also generate similar disease-suppressive activity in this model. Apparently, such suppressive activity is effective in conditions as diverse as $CD4^+$ T helper 1 (Th1)-mediated chronic joint inflammation and the primarily $CD8^+$ T-cell-mediated destruction of insulin-producing T-cells. As such, recognition of self-HSP molecules can be an important immunological strategy that contributes to establishment or maintenance of self-tolerance. The same can be true in the case of inflammation caused by infection, allowing one to logically conclude that the T-cell response to HSPs operates in the control and downmodulation of inflammatory responses, irrespective of their origin.

Immune Responses to HSPs in Arthritis Patients

Immune reactivity toward HSPs has been extensively investigated. For example, when monitoring T-cell proliferative responses to HSP 60 in children with juvenile rheumatoid arthritis (JRA), responses were found to be present exclusively in patients with spontaneously remitting oligoarticular forms (OA-JRA) of the disease but not in patients with progressive (polyarticular or systemic) forms of the disease. Such responses showed a pattern of fluctuation that suggested they coincided with development of remission, i.e. with disease suppression. Analysis of the T cells in these patients revealed the production of interleukin 4 (IL-4) and TGF-beta and overexpression of CD30 upon activation with HSP 60, indicating a Th2-type response. Furthermore, upregulated mRNA levels for IL-4 and IL-10 in the synovium of such HSP 60-responsive patients were observed by reverse transcriptase polymerase chain reaction (RT-PCR).

The majority of such HSP 60-reactive T cells has been found to respond not only to the mycobacterial HSP 60 molecule but especially to the human HSP 60. The presence of such Th2-type cells in the self-remitting forms of the disease suggests the protective nature of these T cells in humans. Various studies have reported on immune reactivity towards HSPs in adult rheumatoid arthritis (RA) patients. Although both humoral and T-cell-mediated responses have been observed, it does not seem that immune responses to HSPs are a general and dominating feature in RA; certainly not in advanced or progressive forms of the disease. However, in an earlier report, it was clearly documented that an RA patient who developed a self-HSP 60 crossreactive T-cell response had a rapidly remitting course of disease. A recent study of T-cell proliferative responses to HSPs in adult RA patients revealed that responses to human HSP 60 were raised upon adding IL-4 in vitro. As this was not observed for responses to mycobacterial HSP 60, it seems that, in agreement with the findings in OA-JRA, recognition of the human (self) molecules preferentially triggers T cells with a regulatory phenotype. Co-culture experiments, in which human HSP 60-specific T-cell lines from RA patients were added to autologous peripheral blood mononuclear cells, have confirmed the regulatory nature of these T cells, as they were found to inhibit tumour necrosis factor alpha production in mononuclear cells derived from RA patients.

HSPs are targets for regulatory T-cell responses. HSPs have unique characteristics which seem to give HSPs a critical immunological status, especially their stress-dependent differential expression. Although strong constitutive expression of HSP 60 has been shown in the thymic medullary epithelium, peripheral T-cell responses to self-HSP are abundant. Thus, self-HSP-specific T cells are probably positively selected and subsequently escape from negative selection, suggesting their receptor has a low affinity for the self-HSP molecule. In the periphery, the level of constitutive expression of HSPs, such as HSP 60, is low and peripheral tolerance for these self-antigens is likely to be less tight than for other, more abundantly available, self-proteins. Under conditions of inflammatory stress, HSP synthesis is grossly upregulated, providing the immune system with a target through which to monitor and control dangerous or potentially deleterious inflammatory conditions.

Several of the characteristic features of HSPs are important. First, their unique degree of evolutionary conservation provides the molecular basis for the demonstrated crossrecognition of microbial and self-HSP by immune cells. Second, microbial HSPs are highly immunogenic and healthy individuals have self-HSP-reactive T cells. Third, HSPs in any cell type, everywhere in the body, respond to a stress by immediate upregulation. Although some of these features may individually be true for other proteins in nature, the combination of the three features are unique for HSPs.

Mechanisms leading to regulation by HSP-reactive T cells.

A number of possible mechanisms may contribute to the regulatory phenotype of self-HSP-reactive T cells at sites of inflammation. Such mechanisms are proposed to be related to the peripheral tolerance mechanisms that are responsible for the persistence and safe containment of self-HSP-reactive T cells in the immune system. First, it is possible that owing to low levels of self-HSP expression in peripheral tissues, self-HSP-specific T cells will simply ignore self-HSP molecules. Only after exposure to microbial HSP, in infection or at the gut mucosa, will these T cells with cross-specificity for conserved microbial HSP epitopes be stimulated and expanded. In the case of autoimmune inflammation, self-HSP expression is upregulated and locally responding T cells will be engaged in low-affinity interactions with self-HSP epitopes. This will lead to a downregulatory IL-4, IL-10, TGF-beta (Th2) phenotype in these cells, producing bystander regulation.

Second, it is possible that the low-level expression of self-HSP epitopes by nonprofessional antigen-presenting cells (APCs) or nonactivated APCs in the periphery, or the conserved microbial HSP epitopes in the 'tolerizing' gut environment, is continuously noted by T cells under normal conditions. This recognition could skew such T cells towards a regulatory phenotype or anergy. Subsequent involvement of these cells at the site of inflammation may promote their regulatory activity, following recognition of overexpressed HSPs on professional APCs. Recently, it has been demonstrated that anergic T cells, generated with antigen in the absence of professional APCs, exerted bystander suppression on the proliferative responses of other T cells in the presence of APC, provided the antigen recognized by the anergic cell was present in the culture. In the case of HSPs, this could mean that quiescent HSP-specific T cells focus their regulatory activity to sites of inflammation where HSPs become temporarily overexpressed. During infection, the activity of such anergic regulators would be outweighed by a dominant frequency of T cells responding (vigorously) to nonconserved microbial HSP epitopes, as well as other microbial epitopes recognized by T cells that are not 'silenced' elsewhere in the periphery.

A third possibility is that self-HSP epitopes are perceived by T cells as APLs or closely related 'partial agonistic' variants of 'full agonist' microbial HSP epitopes. APLs do not fully activate T cells but do have the capacity to trigger certain effector functions such as the production of regulatory cytokines. This could be a profitable strategy in the case of HSPs, since exposure to full agonist microbial HSP epitopes in the gut or during infection would expand the self-HSP or APL-oriented (regulatory) repertoire. During autoimmune inflammation, upregulated self-HSP would serve as the APL inducing a regulatory phenotype in HSP-reactive cells. Although APLs in general may have unpredictable and diverse effects, the fact that in this model the APL-like self-HSP is supposed to be involved in thymic positive selection, generating T cells that have only low affinity interaction with the APL, may give direction (regulatory) to this specific type of APL.

Stimulation of Bone Resorption by Molecular Chaperones

One class of bacterial molecular chaperone, the chaperoning, were recently discovered to be potent inducers of bone resorption (Nair, et al., Calcif Tissue Int 64(3):214-8 (1999). To address the question of whether the osteolytic activity of the chaperonins is unique to this protein class, or is a common attribute of molecular chaperones generally, a number of bacterial and mammalian molecular chaperones have been examined for activity in the murine calvarial bone resorption assay. All the *E. coli* molecular chaperones (groEL, groES, and dnaK) have been found to be active. The osteolytic activity of groEL was inhibited by indomethacin and the natural antagonist of interleukin-1 receptor antagonist (IL-1ra) but was unaffected by neutralization of tumor necrosis factor (TNF) or inhibition of 5-lipoxygenase. Mammalian molecular chaperones of molecular mass 27, 47, 70, and 90 kDa were also tested and, with the exception of the 47 kDa protein, all showed activity in the murine calvarial assay. Molecular chaperones appear, therefore, to have the capacity to modulate the cellular processes in bone explant cultures, resulting in resorption of the calcified matrix.

The methods of treating bone diseases using HSP complexes disclosed herein also encompass adoptive immunotherapy. The HSP complexes can be used to sensitize antigen presenting cells ("APC") and/or macrophage cells. The methods of using Hps complexes to sensitize macrophage and/or APC have been described by U.S. Pat. No. 5,985,270 to Srivastava. The method of adoptive immunotherapy as disclosed therein is thus fully incorporated herein by reference. The APC can be selected from among those antigen presenting cells known in the art, including but not limited to macrophages, dendritic cells, B lymphocytes, and a combination thereof, and are preferably macrophages. The HSP complex-sensitized APC may be administered concurrently or before or after administration of the HSP-antigenic molecule complexes. Adoptive immunotherapy disclosed herein allows activation of antigen presenting cells by incubation in vitro with HSP-antigenic molecule complexes. Preferably, prior to use of the cells in vivo, measurement of reactivity against the bone infectious agent in vitro is done. This in vitro boost followed by clonal selection and/or expansion, and patient administration constitutes a useful therapeutic/prophylactic strategy.

The methods of treating and/or preventing osteoporosis include eliciting an immune response in an individual in whom the treatment or prevention of osteoporosis is desired by administering to the mammalian subject a composition which includes an effective amount of an anti-bacteria composition or a HSP complex. The HSP complex is essentially an HSP noncovalently bound to an antigenic molecule using any convenient mode of administration in combination with the adoptive immunotherapy methods disclosed herein. Modes of administration include but are not limited to subcutaneously, intramuscularly, intravenously, intraperitoneally, intradermally or mucosally.

Therapeutic Dosages

Drug doses are provided in milligrams per square meter of body surface area because this method rather than body weight achieves a good correlation to certain metabolic and excretionary functions (Shirkey, H. C., 1965, JAMA 193: 443). Moreover, body surface area can be used as a common denominator for drug dosage in adults and children as well as in different animal species as indicated below in Table 1 (Freireich, E. J., et al., 1966, Cancer Chemotherap. Rep. 50:219-244).

TABLE 4

Representative Surface Area to Weight Ratios (km) for Various Species[1]

| Species | Body Weight (kg) | Surface Area (Sq m) | km Factor |
|---|---|---|---|
| Mouse | 0.02 | 0.0066 | 3.0 |
| Rat | 0.15 | 0.025 | 5.9 |
| Monkey | 3.0 | 0.24 | 12 |
| Dog | 8.0 | 0.40 | 20 |
| Human, Child | 20 | 0.80 | 25 |
| Adult | 60 | 1.6 | 37 |

Example: To express a mg/kg dose in any given species as the equivalent mg/sq m dose, multiply the dose by the appropriate km factor. In an adult human, 100 mg/kg is equivalent to 100 mg/kg × 37 kg/sq m = 3700 mg/sq m[1] Freireich, et al., 1966, Cancer Chemotherap. Rep. 50: 219–244.

Dosages of the purified complexes of HSPs and antigenic molecules used for administration are preferably much smaller than the dosages estimated by the prior art methods described above. For example, according to a preferred embodiment of the methods disclosed herein, an amount of HSP 70- and/or gp 96-antigenic molecule complexes is administered subcutaneously that is in the range of about 10 micrograms to about 600 micrograms for a human patient, the more preferred human dosage being the same as used in a 25 g mouse, i.e., in the range of 10-100 micrograms. The preferred dosage for HSP-90 peptide complexes in a human patient provided by the methods disclosed herein is in the range of about 50 to 5,000 micrograms, the more preferred dosage being 100 micrograms. Alternatively, in a specific embodiment, an amount of HSP 70- and/or gp 96-antigenic molecule complexes is administered intradermally or mucosally that is in the range of about 0.1 micrograms to about 60 micrograms for a human patient. In another specific embodiment, the therapeutically effective amount of HSP 70- and/or gp 96-antigenic molecule complexes is less than 10 micrograms, e.g., in the range of 0.1 to 9 micrograms; the preferred human dosage being substantially equivalent to or smaller than the dosage used in a 25 g mouse, e.g., in the range of 0.5 to 2.0 micrograms. The preferred dosage for HSP 70-antigenic molecule complexes for intradermal or mucosal administration to a human patient is in the range of about 5 to 500 micrograms. In a specific embodiment, the therapeutically effective amount of HSP 70-antigenic molecule complexes is less than 50 micrograms, e.g., in the range of 5 to 49 micrograms; the preferred dosage being in the range of 5 to 40 micrograms.

In one embodiment, the dosages are administered every other day for a total of five injections. In a preferred embodiment, the doses red above are given once weekly for a period of about 4 to 6 weeks, and the mode of administration is preferably varied with each administration. In a preferred example, each site of administration is varied sequentially. Thus, by way of example and not limitation, the first injection may be given intradermally on the left arm, the second on the right arm, the third on the left belly, the fourth on the right belly, the fifth on the left thigh, the sixth on the right thigh, etc. The same site may be repeated after a gap of one or more injections. Also, split injections may be given. Thus, for example, half the dose may be given in one site and the other half in another site on the same day.

After 4-6 weeks, further injections are preferably given at two-week intervals over a period of time of one month. Later injections may be given monthly. The pace of later injections may be modified, depending upon the patient's clinical progress and responsiveness to the immunotherapy. Alternatively, the mode of administration is sequentially varied, e.g., weekly administrations are given in sequence intradermally or mucosally.

The above regimens for administration of HSP-antigenic molecule complexes may occur before, during or after administration of the HSP-antigenic molecule complex-sensitized APC. For example, the mode of therapy can be sequentially varied, e.g., HSP-antigenic molecule complexes may be administered at one time and HSP-antigenic molecule-sensitized APC another time. Alternatively, HSP-antigenic molecule complexes may be administered concurrently with HSP-antigenic molecule-sensitized APC. Preferably, the APC and complexes are administered to the patient within 1 week of each other.

Kits of the compositions disclosed herein include in a first container a pharmaceutical composition comprising a complex of a HSP noncovalently bound to an antigenic molecule and a pharmaceutically acceptable carrier; and in a second container antigen presenting cells. HSP-antigenic molecule complexes may be formulated into pharmaceutical preparations for administration as described above. Compositions may include a compound formulated in a compatible pharmaceutical carrier prepared, packaged, and labeled for treatment of the indicated bone infectious disease. Alternatively, pharmaceutical compositions may be formulated for treatment of appropriate bone infectious diseases.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Kits for carrying out the therapeutic regimens disclosed herein are also provided. Such kits comprise in a first one or more containers therapeutically or prophylactically effective amounts of the HSP-antigenic molecule complexes, preferably purified, in pharmaceutically acceptable form; and in a second container the sensitized APC, preferably purified. The HSP-antigenic molecule complex in a vial of a kit may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for injection purposes.

In another embodiment, a kit disclosed herein further comprises a needle or syringe, preferably packaged in sterile form, for injecting the complex, and/or a packaged alcohol pad. Instructions are optionally included for administration of HSP-antigenic molecule complexes by a clinician or by the patient.

The methods and the compositions and the use thereof an be better understood by the following non-limiting examples.

EXAMPLE 1

Experimental

Bone samples obtained from healthy and compromised subjects were weighed and transferred to 50 ml Falcon tubes. Phosphate buffer saline (PBS) were added to the bone samples to obtain a weight (g) to volume (ml) ratio of 0.4+0.2. Samples were agitated and partially ground using the "Tissue Tearer" at rotor setting 1 (4500-8000 rpm) for 1 minute and rotor setting 3 (12,000-17,000 rpm) for another minute. To increase extraction efficiency, the bone samples were stored in Falcon tubes for 9 days at 4° C. Lipids and large debris were avoided as 1 ml of each sample are transferred to an Eppendorf tube. Any debris were cleared out by centrifuging the samples at 15,000 rpm for 10 minutes.

The samples were analyzed using first SDS-PAGE, then the Protein 200 Assay on the Agilent 2 100 Bioanalyzer. Some samples that did not produce satisfactory results (often indicated by a missing upper marker) were desalted and rerun on the Bioanalyzer. Samples were desalted by using YM-3 Centricon tubes spun at 4200×g for approximately 1.5 hours. The Centricon filters were inverted and spun at 1000×g for 3 minutes. The samples were reconstituted to their original volume with 22 mM Tris.

Results

A SDS-PAGE was conducted on bone extracts from a control healthy patient. Slab gel electrophoresis of samples against a ladder of known proteins suggested good separation. The Protein 200 assay was then used with the Bioanalyzer with a series of extracts. The results show the stronger presence of bands in the 45-65 kDa range for samples obtained from compromised patents. Because the presence of salts is known to interfere with the assay and that the extracts used in this study were produced in phosphate buffer saline solution, a follow-up experiment was designed to address the potential salt problem. First, a filtration step was added to remove salts from the samples. Furthermore, extraction was conducted with deionized water, instead of with PBS. The changes yielded an improved separation, and the upper marker became visible in some of the samples.

This study provided two methods for identifying proteins in bone extracts: the traditional SDS-PAGE gel electrophoresis and the Protein 200 Chip Assay. The latter technique is more sensitive than the former and this could be beneficial in detecting proteins produced at low levels. The data indicates there is an association between compromised bone sampler and electrophoretic bands in the 45-65 kDa region.

Immunoblotting

Samples separated on one-or two-dimensional SDS-PAGE will be electroblotted onto hnmobilon P. polyvinyldifluoride membranes (Millipore Corp., Bedford, Mass.) overnight (Laemmli, 1970). Membranes will be washed with PBS containing 0.1% Triton X-100 (Sigman Immunochemicals) (PBS-T) and blocked with PBS-T containing 2% FCS (blocking buffer) SeraLab). Blocked membranes will then be incubated with the test antibody (in blocking buffer) for 1 hr. and washed with PBS-T. Bound test-antibody (anti-mouse) IgG (gamma-chain specific) (Sigma Immunochemicals) at 1:1,000 in PBS-T2% FCS. After a final wash the blots will be developed with a solution of 1 mg/ml 3,3 prime-diaminobenzidine tetrahydrochloride (Sigma Immunochemicals) in 50 mM Tris (Sigma Immunochemicals), pH 7.6, containing 150 mM NaCl (BDI-I) and 0.05% hydrogen peroxide (Sigma Immunochemicals). Each reaction will be terminated by extensive rinsing with distilled water.

Protein purification

Crude BS will be fractionated at 4" C on a Q-Sepharose anion exchange column (50 cm times 1.6 cm). The column will be equilibrated in 20 mM Tris-HCl, pH 8.5 (buffer A), and the BS (generally 100400 mg) will be loaded on in the same buffer. The column will be washed with 500 ml of buffer A and then eluted with a 1,000-ml linear gradient of 0-1 M NaCl in buffer A. Ten-ml fractions will be collected, and the absorbence at 280 nm will be monitored. The location of the osteolytic chaperone protein will be determined by a combination of activity assay, SDS-PAGE, and the Western blot analysis. Fractions containing osteolytic activity will be dialyzed against deionized water to remove salt and lyophilized. The fraction with the highest specific activity and the least number of protein bands on SDS-PAGE will then be further fractionated at room temperature on a second anion exchange column.

The purity of the fractions will again be assessed visually by SDS-PAGE and 100 pg of the cleanest fraction will be dialyzed against 50 mM of Tris buffer, pH 7.6 containing 10 mM MgC12 (buffer C). This sample will be run on a 5-ml ATP-Sepharose (Sigma Immunochemicals) column. The column will be washed with 10 column volumes of butter C and bound protein eluted in 5 column volumes of a5mM ATP (Sigma Immunochemicals), also in buffer C. Protein will be located by SDS-PAGE and visualized using a silver stain kit (Sigma Immunochemicals). Gel filtration will be used to determine the molecular mass range of the osteolytic chaperone protein isolated by ATP-affinity chromatography. This will be done by running the purified protein on a Bio-Sil TSK250 (Bio Rad Laboratories) column in 0.1 M sodium phosphate buffer, pH 6.7, and measuring absorption at 205/280 nm.

Specific Aim #3: Data analysis and correlation to clinical outcome variables

The experimental findings and clinical bone densitometry and Q-CT measurements will be documented with the use of a standardized relational computer database using a numerical code system. The computer program SPSS/PC+9.0 (SPSS Inc., 44 N. Michigan Ave., Chicago, Ill. 60611) will be used for statistical analysis of the compiled data. Descriptive statistics of the raw data will be done with the use of frequency tables. Normal distribution will be determined by fitting to normality and by obtaining normal probability plots, where the ranked observed residuals (deviation from the mean) are plotted on the x-axis against the standardized values of the normal distribution on the y-axis. Normal distribution is indicated if the observed residuals fall onto the straight line. Significant differences between means were evaluated with the use of a T-test for dependent and independent samples, and one-way ANOVA analysis of variance. In case of a statistically significant F-Test from an ANOVA using multivariate variables, the contributing means will be differentiated by post-hoc comparison using a Tukey HSD test for unequal sample sizes. The use of the latter two tests will allow to determine the occurrence of the various Chaperone Molecules and the presence of an osteopenic bone sample according to the patients age and gender and other concomitant medical conditions. In essence, this test will allow us to identify the predominant chaperone molecule correlating with osteopenia.

A cross tabulation method will be used to measure the relationships between osteopenia, age, gender, other contributing factors, and the presence of chaperone molecules by generating multiple-way frequency tables. For each possible combination of these variables, these tables yield a cell frequency, i.e., the number of cases in the patient population that had this particular combination. In addition, the cross tabulation method will allow to evaluate the reliability of the test, in other words, the statistical significance of these relationships. Hence, the presence of osteopenia, age, gender, other contributing factors such as medical conditions are categorical variables. Multiple simultaneous relations and interactions between the variables of the multipleway frequency table will be examined on the basis of log-linear equations, which allow computation of the cell frequencies that would have been expected if the variables involved were unrelated. This will be done with the use of an interactive proportional fitting procedure. Thus, significant deviations of the observed from the expected frequencies will reflect a statistically significant relationship between a specific chaperone molecule and osteopenia. Significance testing of deviations of the observed from the expected frequencies will be done via a Pearson Chi-square test. The residual frequencies will be calculated by subtracting the expected frequencies from the observed frequencies. If no relationship exists, all residual frequencies are expected to consist of positive and negative values of similar magnitude and to be evenly distributed across the cells of the frequency table. Plotting the residuals is therefore used as another means of assessing correlations between the presence of chaperone molecules with osteopenia. In all statistical tests employed in this study, a significance level of $p<0.05$ will be chosen.

We claim:

1. A method of detecting osteoporosis in an individual to be tested comprising:
   a) obtaining a sample of a bone related tissue or cells;
   b) assaying a concentration of at least one marker selected from the group consisting of
      (i) a bacteria is selected from the group consisting of *Staphylococcus aureus, Porphyromonas gingivallis, Eikenella corrodens, Acrinobacilus actinomycetemcomitans, Prevotella intermedia, Campylobacter rectus, Staphylococcus epidermidis, Salmonella* spp., *Neisseria gonorrhoea, NeisseHa meningitis, Myeobacterial tuberculosis, Haemophius influenzae, Pasteurella multocida, B. bronchiseptica,* and *Fusobacterium nucleatum,*
      (ii) a bacterially produced factor selected from the group consisting of endotoxin-LPS, gapstatin, and dermonecrotic toxin (DNT), and
      (iii) a heat shock protein (HSP) produced in response to an infectious agent, the HSP selected from the group consisting of HSP 60, gp 96, cpn20, ubiquitin, and cpn 30; and
   c) comparing the concentration of the at least one marker with the concentration of the marker in a sample of the same bone related tissue or cells from a control individual who does not have osteoporosis.

2. The method of claim 1 further comprising comparing the concentration of a first marker with concentrations of a same marker obtained from the same individual over a period of time.

3. The method of claim 2 wherein the time period is at least about 12 hours.

4. The method of claim 1 wherein the sample comprises bone cells or body fluid.

5. The method of claim 1 wherein the HSP is HSP 60.

6. The method of claim 1 wherein the HSP is ubiquitin.

7. The method of claim 1 wherein the concentration of HSP is measured using an immunoassay.

8. The method of claim 1 wherein the concentration of HSP is measured using an assay for a nucleotide molecule encoding HSP.

9. The method of claim 1 wherein the factor is selected from the group consisting of gapstatin and dermonecrotic toxin.

10. The method of claim 1 wherein the factor is gapstatin.

11. The method of claim 1 wherein the factor is dermonecrotic toxin.

12. The method of claim 1 wherein the bacteria is selected from the group consisting of *Staphylococus aureus, Actinobacillus actinomycetemcomitans, Bordetella bronchiseptica,* and *Fusobacerium nucleatum.*

* * * * *